United States Patent
Rao et al.

(10) Patent No.: US 6,642,407 B2
(45) Date of Patent: Nov. 4, 2003

(54) PRODUCTION, PURIFICATION AND POLYMERIZATION OF AROMATIC DICARBOXYLIC ACIDS

(75) Inventors: Krishna Kulai Rao, Kingwood, TX (US); Russell D. Sellen, Beaumont, TX (US); Xiaobing Feng, League City, TX (US); James Spanswick, Wheaton, IL (US); William F. Huber, Jr., Naperville, IL (US)

(73) Assignee: Exxon Mobil Chemical Patents Inc., Houston, TX (US)

( * ) Notice: Subject to any disclaimer, the term of this patent is extended or adjusted under 35 U.S.C. 154(b) by 0 days.

(21) Appl. No.: 10/133,083

(22) Filed: Apr. 26, 2002

(65) Prior Publication Data

US 2002/0173674 A1 Nov. 21, 2002

Related U.S. Application Data

(63) Continuation of application No. 09/860,275, filed on May 18, 2001, now abandoned.

(51) Int. Cl.[7] .......................... C07C 67/48; C07C 69/76; C07C 51/16; C07C 51/255
(52) U.S. Cl. .................... 560/79; 560/89; 560/91; 562/414
(58) Field of Search ................. 560/79, 80, 100, 560/89, 96, 91; 562/407, 409, 485, 487, 494

(56) References Cited

U.S. PATENT DOCUMENTS

| | | | |
|---|---|---|---|
| 3,299,125 A | 1/1967 | Ickikawa | 260/524 |
| 3,639,451 A | 2/1972 | Ebert | 260/475 R |
| 3,650,907 A * | 3/1972 | McNelis et al. | 203/96 |
| 3,697,579 A | 10/1972 | Balint et al. | 260/468 R |
| 3,953,535 A | 4/1976 | Shima et al. | 260/668 |
| 4,162,991 A | 7/1979 | Jones | 252/413 |
| 4,317,924 A | 3/1982 | Cahen | 562/487 |
| 4,334,086 A | 6/1982 | Hanotier et al. | 562/413 |
| 4,745,211 A | 5/1988 | Jackson, Jr. et al. | 560/80 |
| 4,950,825 A | 8/1990 | Sikkenga et al. | 585/320 |
| 5,023,390 A | 6/1991 | Abe et al. | 585/320 |
| 5,262,560 A | 11/1993 | Holzhauer et al. | 560/78 |
| 5,374,707 A | 12/1994 | Asrar et al. | 528/272 |
| 5,587,508 A | 12/1996 | Machida | 560/77 |
| 5,847,070 A | 12/1998 | Asrar et al. | 528/272 |
| 5,872,284 A | 2/1999 | Iwasaki et al. | 562/486 |
| 6,100,374 A | 8/2000 | Iwasaki et al. | 528/483 |
| 6,114,575 A | 9/2000 | McMahon | 562/414 |
| 6,121,501 A | 9/2000 | Motoyuki et al. | 585/323 |

FOREIGN PATENT DOCUMENTS

| | | | |
|---|---|---|---|
| JP | 54-98706 | * | 8/1979 |
| WO | 93/12065 | | 6/1993 |
| WO | 93/18062 | | 4/1999 |

* cited by examiner

*Primary Examiner*—Mukund J. Shah
*Assistant Examiner*—Zachary C. Tucker
(74) *Attorney, Agent, or Firm*—Darryl M. Tyus; Linda A. Kubena (57) ABSTRACT

This invention provides a process for purifying the crude aromatic dicarboxylic acids produced by oxidation of dialkyl aromatic hydrocarbons and for using the purified acids in the preparation of polyethylene terephthalate, polyethylene naphthalate and other polyesters. The invention simplifies the manufacturing process by converting the crude aromatic acids into bis-glycol esters in an esterification reactor 4, from which the esterified partial oxidation impurities present in the oxidation product are removed by distillation in distillation tower 5. After removal of the volatile impurities, the dicarboxylic acid esters can separated by distillation in distillation tower 6 or by crystallization and converted to polyesters by polycondensation. The volatile impurities removed as overhead from tower 5 can be recycled as stream 16 to the oxidation reactor where they act as oxidation promoters thereby optionally allowing for a bromine-free oxidation process for dialkyl aromatic hydrocarbons.

19 Claims, 4 Drawing Sheets

PRODUCTION, PURIFICATION AND POLYMERIZATION OF AROMATIC DICARBOXYLIC ACIDS

This application is a continuation of U.S. Ser. No. 09/860,275, filed May 18, 2001 now abandoned.

BACKGROUND OF THE INVENTION

1. Field of the Invention

This invention relates to the production, purification and polymerization of aromatic dicarboxylic acids for use in the preparation of polyesters. In particular, the invention relates to processes for producing and purifying crude terephthalic acid and 2,6-naphthalenedicarboxylic acid and for using the purified acids in the production of polyethylene terephthalate (PET) and polyethylene naphthalate (PEN).

2. Description of the Prior Art

Polyesters are polymers typically prepared by polycondensation reactions starting from polycarboxylic acids and polyols. The polyesters of greatest commercial interest are those based on the reaction products of terephthalic acid and 2,6-naphthalenedicarboxylic acid with aliphatic diols, with the preferred diol being ethylene glycol. The first commercial polyester was polyethylene terephthalate (PET). However, more recently significant attention has been focused towards polyethylene naphthalate (PEN), because fibers and films made from PEN have improved strength and thermal properties relative to, for example, fibers and films made from PET. High strength fibers made from PEN can be used to make tire cord, and films made from PEN are advantageously used to manufacture magnetic recording tape and electronic components. Also, because of its superior resistance to gas diffusion, and particularly to the diffusion of carbon dioxide, oxygen and water vapor, films made from PEN are useful for manufacturing food containers, particularly so-called "hot fill" type food containers. Polyesters made from mixtures of terephthalic acid and 2,6-naphthalenedicarboxylic acid or dimethyl-2,6-naphthalenedicarboxylate also have been found to have unique and desirable properties such as resistance to gas diffusion, making them suitable for manufacturing, for example, beverage containers or other containers for food products, including containers for beer.

Polyester resin is most often presently prepared by forming a slurry of the purified aromatic dicarboxylic acid, or the dimethylester of the aromatic dicarboxylic acid, and ethylene glycol, in the presence of an esterification catalyst such antimony, and subjecting the mixture to successively higher temperature and lower pressures to drive out the condensation products; and then, in the presence of a polyesterification catalyst the excess ethylene glycol is removed under reduced pressure to bring the molecular weight to the desired range. The current polyester production process involves at least three steps. In the first step, esterification of the acid with excess glycol (or transesterification if the methyl esters are used), the bulk of the water or methanol is removed. The diglycol ester then passes to the second, prepolymerization step to form intermediate molecular weight oligomers before passing to the third, melt polyesterification step operated at low pressure and high temperature. For some applications requiring higher melt viscosity a further solid-state polymerization is practiced.

As will be discussed in more detail below, current processes for the preparation of terephthalic acid and 2,6-naphthalenedicarboxylic acid involve catalytic oxidation of p-xylene or 2,6-dimethylnaphthalene and provide a crude oxidation product which contains, as major impurities, mono-carboxylic acids, tricarboxylic acids, such as trimellitic acid, and aldehydes produced as oxidation by-products, together with residues, such as cobalt, manganese and bromine, derived from the oxidation catalyst. However, it is well known that, when used as starting materials for the manufacture of polyester fibers and films, dicarboxylic acids must achieve a high degree of purity, since the presence of contaminants, even in minute amounts, can have deleterious effects upon the quality of the resulting resin. For instance, in the case of terephthalic acid, monocarboxylic acid oxidation intermediates, such as p-toluic acid and/or 4-carboxybenzaldehyde, may react with ethylene glycol when present in the polycondensation reaction mixture and therefore act as chain stoppers, with the consequence that the melting point and strength of the resulting polyester may be substantially and undesirably lowered. Moreover, the impurities present in the crude acid can result in discoloration of the PET or PEN resin, as well as mold staining during the molding process, thereby decreasing the transparency of the molded products and hence lowering the product quality.

Thus, in order to obtain high-quality, high molecular weight PET and PEN, the crude dicarboxylic acid needs to be purified before it is used as a starting material for preparing polyesters. Several processes have been proposed for the purification of crude terephthalic acid and naphthalene dicarboxylic acid and are described below.

For example, U.S. Pat. No. 4,317,924 discloses a process for purifying crude terephthalic acid by treating a suspension of the crude acid in an aqueous solution of a water-soluble heavy metal salt with nitrogen and/or hydrogen in the presence of a supported noble metal catalyst under conditions sufficient to reduce the 4-carboxybenzaldehyde impurity without significant reduction of the terephthalic acid. The treated solution is then separated from the catalyst and the purified crystalline terephthalic acid is recovered by crystallization.

U.S. Pat. Nos. 6,100,374 and 5,872,284 describe a process of purifying crude naphthalene dicarboxylic acid comprising the steps of mixing crude naphthalene dicarboxylic acid and an ethylene glycol aqueous solution, heating the resulting mixture to esterify part of the naphthalene dicarboxylic acid and thereby give a naphthalene dicarboxylic acid ester and dissolving the naphthalene dicarboxylic acid ester in the ethylene glycol aqueous solution; then contacting impurities, which are contained in the crude naphthalene dicarboxylic acid and capable of being hydrogenated, with hydrogen in the presence of a hydrogenation catalyst to hydrogenate the impurities and dissolving the hydrogenated impurities in the ethylene glycol aqueous solution; and subsequently crystallizing the naphthalene dicarboxylic acid ester and separating the resulting crystals from the ethylene glycol aqueous solution containing the soluble impurities.

U.S. Pat. No. 4,745,211 and Japanese Patent Laid-Open Publication No. 110650/1989 describe methods of purifying crude naphthalenedicarboxylic acid comprising the steps of causing impure 2,6-naphthalenedicarboxylic acid to react with ethylene glycol in an amount of at least 2 mol based on 1 mol of the 2,6-naphthalenedicarboxylic acid in the presence of catalytic amounts of a tertiary amine and an added titanium-containing compound as an esterification catalyst to prepare bis(2-hydroxyethyl) 2,6-naphthalenedicarboxylate; crystallizing the bis(2-hydroxyethyl) 2,6-naphthalenedicarboxylate; and recovering the purified bis(2-hydroxyethyl) 2,6-naphthalenedicarboxylate by crystallization. No impurities are removed by distillation.

Another method of purifying crude naphthalene dicarboxylic acid, optionally employing diglycol esters, is disclosed in U.S. Pat. No. 6,100,374 and comprises the steps of mixing crude naphthalene dicarboxylic acid and an alcohol aqueous solution, heating the resulting mixture to esterify a part of the naphthalene dicarboxylic acid and thereby give a naphthalene dicarboxylic acid ester, dissolving the naphthalene dicarboxylic acid ester in the alcohol aqueous solution; then contacting aldehydes, which are contained in the crude naphthalene dicarboxylic acid, with a sulfite to give aldehyde adducts and dissolving the aldehyde adducts in the alcohol aqueous solution; and subsequently crystallizing the naphthalene dicarboxylic acid and the naphthalene dicarboxylic acid ester and separating the resulting crystals from the alcohol aqueous solution.

U.S. Pat. No. 5,262,560 describes a process for purifying 2,6-naphthalenedicarboxylic acid which proceeds by preparing and purifying dimethylnaphthalene dicarboxylate. In particular, the process comprises the steps of: causing 2,6-naphthalenedicarboxylic acid to react with methanol in an appropriate reaction region to prepare a reaction mixture containing dissolved dimethyl 2,6-naphthalenedicarboxylate and monomethyl 2,6-naphthalenedicarboxylate; cooling the reaction mixture to a temperature of not higher than about 40° C. to crystallize major parts of the dissolved dimethyl 2,6-naphthalenedicarboxylate and monomethyl 2,6-naphthalenedicarboxylate; fractionating the thus crystallized dimethyl 2,6-naphthalenedicarboxylate and monomethyl 2,6-naphthalenedicarboxylate from the reaction mixture solution; heating the thus fractionated dimethyl 2,6-naphthalenedicarboxylate and monomethyl 2,6-naphthalenedicarboxylate in a recrystallization solvent to a temperature high enough to dissolve at least a part of the dimethyl 2,6-naphthalenedicarboxylate and substantially all of the monomethyl 2,6-naphthalenedicarboxylate; recrystallizing the dimethyl 2,6-naphthalenedicarboxylate, which has been dissolved in the recrystallization solvent, at a temperature at which a major part of the monomethyl 2,6-naphthalenedicarboxylate is held in the recrystallization mother liquor; and fractionating the thus recrystallized dimethyl 2,6-naphthalenedicarboxylate from the recrystallization mother liquor.

Japanese Patent Laid-Open Publication No. 173100/1995 describes a process for preparing high-purity 2,6-naphthalenedicarboxylic acid comprising the steps of dissolving coarse crystals of impurity-containing 2,6-naphthalenedicarboxylic acid in water in a supercritical or subcritical state; cooling the resulting solution to a temperature of not higher than 300° C. to precipitate the acid crystals; and separating the purified crystals from the mother liquor at a temperature of 100 to 300° C.

In addition to the problems involved in purifying the crude terephthalic acid and naphthalene dicarboxylic acid, the oxidation process used to produce the crude acid has also been the subject of considerable research. Thus, existing oxidation processes for the production of terephthalic acid and 2,6-naphthalene dicarboxylic acid normally involve dissolving the para-xylene or 2,6-dimethylnaphthalene in an aliphatic carboxylic acid, such as acetic acid, and then treating the solution with molecular oxygen in the presence of a suitable catalyst. Typically, such catalysts include mixtures of cobalt and manganese promoted with bromine. However the presence of both bromine and acetic acid at the high reaction temperature involved makes the system highly corrosive, requiring the use of titanium and high nickel alloys throughout the plant and thereby increasing the equipment costs.

For example, U.S. Pat. No. 6,114,575 describes a process for preparing 2,6-naphthalenedicarboxylic acid by the liquid phase, exothermic oxidation of 2,6-dimethylnaphthalene comprising adding to a reaction zone oxidation reaction components comprising 2,6-dimethylnaphthalene, a source of molecular oxygen, a solvent comprising an aliphatic monocarboxylic acid, and a catalyst comprising cobalt, manganese and bromine components wherein the atom ratio of cobalt to manganese is at least about 1:1 and the total of cobalt and manganese, calculated as elemental cobalt and elemental manganese added to the reaction zone, is less than about 0.40 weight percent based on the weight of the solvent added to the reaction zone; maintaining the contents of the reaction zone at a temperature and pressure sufficient to cause the oxidation of 2,6-dimethylnaphthalene to 2,6-naphthalenedicarboxylic acid and the vaporization of at least a portion of the reaction solvent while maintaining a liquid phase reaction mixture; condensing the vaporized solvent and returning an amount of the condensed solvent to the reaction zone to maintain the amount of water in the reaction zone at no more than about 15 weight percent based on the weight of solvent in the reaction zone; and withdrawing from the reaction zone a mixture comprising 2,6-naphthalenedicarboxylic acid.

However, during the liquid phase oxidation of 2,6-dimethylnaphthalene to 2,6-naphthalenedicarboxylic acid using bromine-promoted catalysts, such as described in U.S. Pat. No. 6,114,575, various unwanted by-products are usually produced. For example, trimellitic acid (TMLA) is produced by the oxidation of one of the rings of the 2,6-dimethylnaphthalene molecule. 2-Formyl-6-naphthoic acid (FNA), a result of incomplete oxidation of one of the methyl groups of the 2,6-dimethylnaphthalene molecule, is also produced. In the presence of bromine, as an oxidation promoter, bromination of the naphthalene ring occurs during the oxidation reaction and results in the formation of bromonaphthalene dicarboxylic acid (BrNDA). Additionally, loss of one methyl (or carboxylic acid) substituent during the oxidation reaction results in the formation of 2-naphthoic acid (2-NA). These and other unidentified by-products are undesirable because they contaminate the 2,6-naphthalenedicarboxylic acid.

To obviate the problems associated with bromine-promoted oxidation catalysts, various proposals have been made for bromine-free oxidation processes. For example, U.S. Pat. No. 4,334,086 discloses the bromine-free oxidation of p-xylene to terephthalic acid in the presence of not more than about 10 weight % of water and a catalyst comprising a mixture of cobalt and manganese salts, wherein aldehyde/acid impurities comprising partially oxidized species are recycled as oxidation promoters.

Recycling of some naphthalate esters to the oxidation step is disclosed in U.S. Pat. No. 5,587,508 wherein high boiling residues from the distillation of dimethyl-2,6-naphthalenedicarboxylate are used as additives in the oxidation of 2,6-dimethylnaphthalene. The process continues to teach the use of a bromine as promoter in the oxidation and teaches that the only advantage to recycle of the crude methyl ester residues is to increase the particle size of the precipitating crude 2,6-naphthalenedicarboxylic acid thereby expediting filtration.

According to the present invention, it has been found that crude aryldicarboxylic acids can be purified by esterification followed by distillation without any intervening chemical treatment such as hydrogenation or treatment with sulfite. In particular, it has been found that the esterified partial oxidation products formed during the esterification process have significantly lower boiling points than the esters of the dicarboxylic acid and hence can readily be separated by distillation. The resultant purified dicarboxylic acid esters can then be subjected to direct polyesterification to produce the required polyester resin. In addition, it has been found that the esterified partial oxidation impurities distilled from the esterification effluent can be recycled to the oxidation reactor where they act as oxidation promoters thereby optionally allowing for a bromine free oxidation process for substituted aryl hydrocarbons.

The preparation of pure diglycol esters of 4,4-biphenyl dicarboxylic acid is addressed in U.S. Pat. Nos. 5,374,707 and 5,847,070. While these patents demonstrate the utility of pure glycol esters, with low levels of diethylene glycol, in mixed polyesterification reactions, the process starts with pure dicarboxylic acids and addresses only the reduction in the level of diethylene glycol produced in the esterification process. The patents do not teach the use of diglycol esters in the purification of aromatic dicarboxylic acids.

SUMMARY OF THE INVENTION

In accordance with one aspect of the invention, there is provided a process for purifying an aryldicarboxylic acid, comprising the steps of:

i) reacting the crude aryldicarboxylic acid with a glycol to esterify at least part of the aryldicarboxylic acid and produce an esterification effluent containing an aryldicarboxylic acid ester;

ii) removing volatile impurities from said esterification effluent by distillation; and iii) after step (ii), separating the aryldicarboxylic acid ester from said esterification effluent.

Preferably, the crude aryldicarboxlic acid is first produced by the additional steps of (iv) oxidizing a disubstituted aryl hydrocarbon in the presence of a transition metal catalyst to prepare a mixture comprising said crude aryldicarboxylic acid; and (v) separating the crude aryldicarboxylic acid from said mixture.

Preferably, at least part of the volatile impurities removed in step (ii) is recycled to step (iv) to act as an oxidation promoter.

In accordance with a further aspect of the invention, there is provided a process for purifying naphthalenedicarboxylic acid, comprising the steps of:

i) mixing crude naphthalenedicarboxylic acid with an aqueous solution of an alcohol;

ii) heating the mixture produced in step (i) to esterify a part of the naphthalenedicarboxylic acid and thereby give a naphthalenedicarboxylic acid ester, and iii) dissolving the naphthalenedicarboxylic acid ester produced in step (ii) in the aqueous alcohol solution;

iv) then reducing the pressure of the aqueous alcohol solution to remove volatile species; and v) subsequently crystallizing the naphthalenedicarboxylic acid ester from the aqueous alcohol solution and separating the resultant crystals from the aqueous alcohol solution.

In accordance with yet a further aspect of the invention, there is provided a process for preparing polyethylene naphthalate, comprising the steps of:

i) oxidizing 2,6-dimethylnaphthalene to produce an oxidation effluent comprising crude naphthalene dicarboxylic acid;

ii) separating the crude naphthalene dicarboxylic acid from said oxidation effluent;

iii) optionally, washing the crude naphthalene dicarboxylic acid with aqueous acetic acid;

iv) mixing the separated crude naphthalene dicarboxylic acid with an aqueous solution of ethylene glycol;

v) heating the resulting mixture to esterify at least part of the naphthalene dicarboxylic acid and thereby produce a naphthalene dicarboxylic acid ester;

vi) dissolving the naphthalene dicarboxylic acid ester in the aqueous glycol solution;

vii) then distilling the aqueous glycol solution produced in step (vi) to remove volatile impurities;

viii) subsequently separating the naphthalene dicarboxylic acid ester from the aqueous glycol solution remaining after step (vii), and ix) subjecting the naphthalene dicarboxylic acid ester separated in step (viii) to a polycondensation reaction.

DESCRIPTION OF SPECIFIC EMBODIMENTS

For the sake of simplicity, the present invention will now be more particularly described with reference to the preparation of polyesters incorporating 2,6-naphthalenedicarboxylic acid residues prepared by oxidation of 2,6-dimethylnaphthalene. However, it is to be appreciated that the process described is equally applicable to the production of polyesters based on other aromatic carboxylic acids, such as PET.

Figure 2:
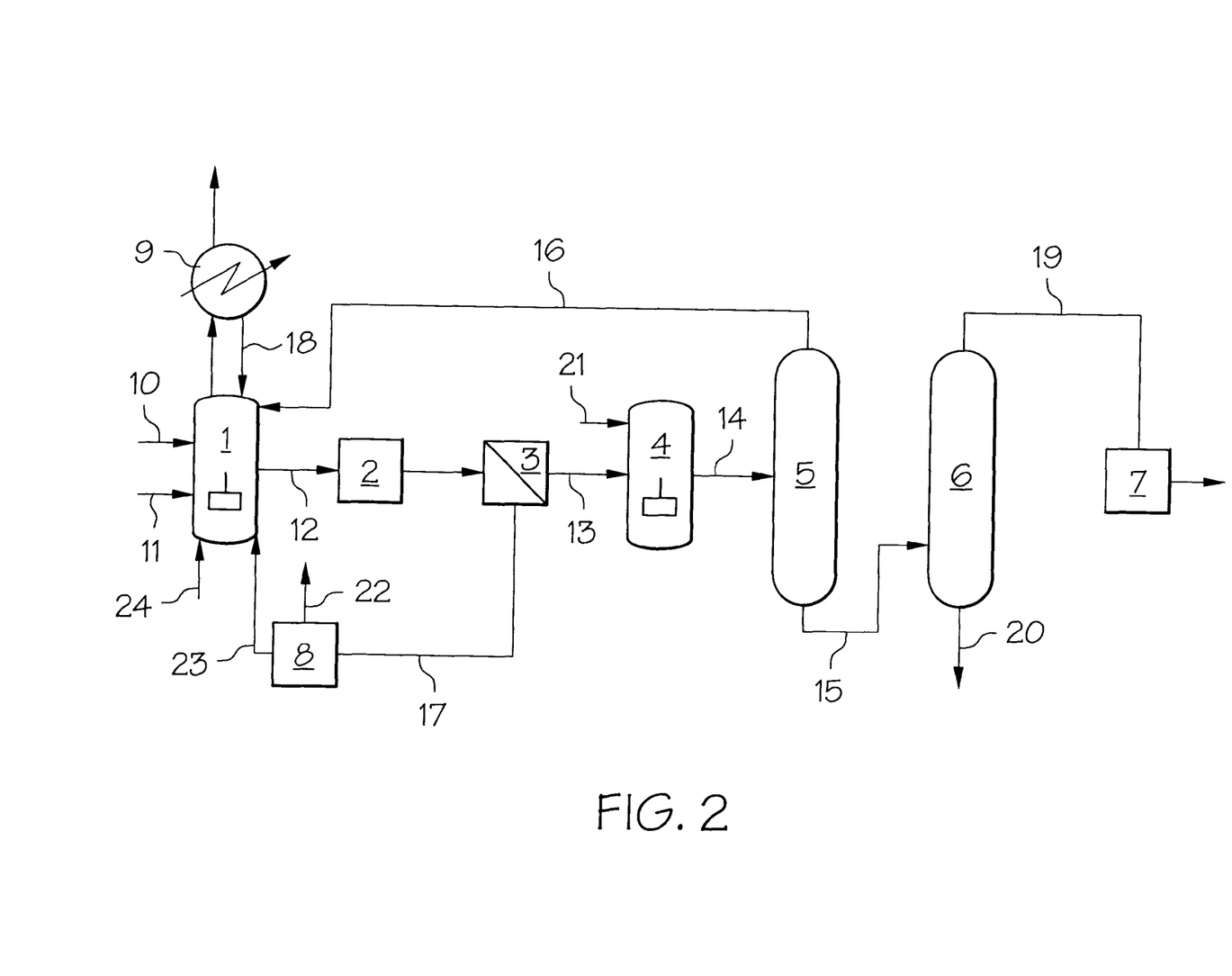
FIG. 2 is a flow sheets for a process, in accordance with one example of the invention, for the oxidation of 2,6-dimethylnaphthalene to crude 2,6-naphthalene dicarboxylic acid, purification of the crude acid through esterification with a diol and polyesterification of the bis-glycol ester of 2,6-naphthalene dicarboxylic acid.

One embodiment of the invention is shown in FIG. 2, wherein 2,6-dimethylnaphthalene (stream 10), air (stream 24), acetic acid (stream 23) and an oxidation promoter (stream 11) are fed to an oxidation reactor 1 where the 2,6-dimethylnaphthalene is oxidized in the presence of a transition metal catalyst to produce an effluent stream 12 containing crude 2,6-naphthalenedicarboxylic acid. The oxidation reaction is exothermic and the heat generated in reactor 1 is removed by heat exchanger 9 with condensed liquid recycled to the reactor 1 as stream 18. The effluent stream 12 from the reactor 1 is fed to a crystallizer vessel 2 where the stream 12 is cooled so as to crystallize the crude naphthalenedicarboxylic acid. The cooled oxidation effluent is then fed to a solid/liquid separator 3 where the naphthalenedicarboxylic acid crystals are separated from the acetic acid mother liquor by filtration and then washed. The separated acid crystals are then fed as stream 13 to esterification reactor 4 whereas the mother liquor is fed as stream 17 to a separation tower 8 where the water is removed as stream 22 before the acetic acid is recycled to reactor 1. In the reactor 4, the naphthalenedicarboxylic acid is reacted with monoethylene glycol fed to reactor 4 as stream 21 in the presence of oxidation catalyst residues retained by the acid to produce a diglycol ester of 2,6-naphthylene dicarboxylic acid. The ester is then fed as stream 14 for purification in series-connected distillation towers 5 and 6. Volatile esterified impurities, such as 6-formyl-2-naphthoic acid ester, are removed by distillation in the first distillation tower 5 and are recycled to the oxidation reactor as stream 16 to act as an oxidation promoter. The residue from tower 5 is then fed as stream 15 to the second distillation tower 6, where the purified diglycol ester of 2,6-naphthylene dicarboxylic acid is removed as overhead stream 19. Heavy byproducts from the tower 6 are removed as stream 20 and may be partially recycled to either oxidation or esterification reactors or disposed of as waste. The purified glycol ester stream 19 may be condensed and flaked in product cooler 7 or used directly as starting material for preparing PEN.

Figure 3:
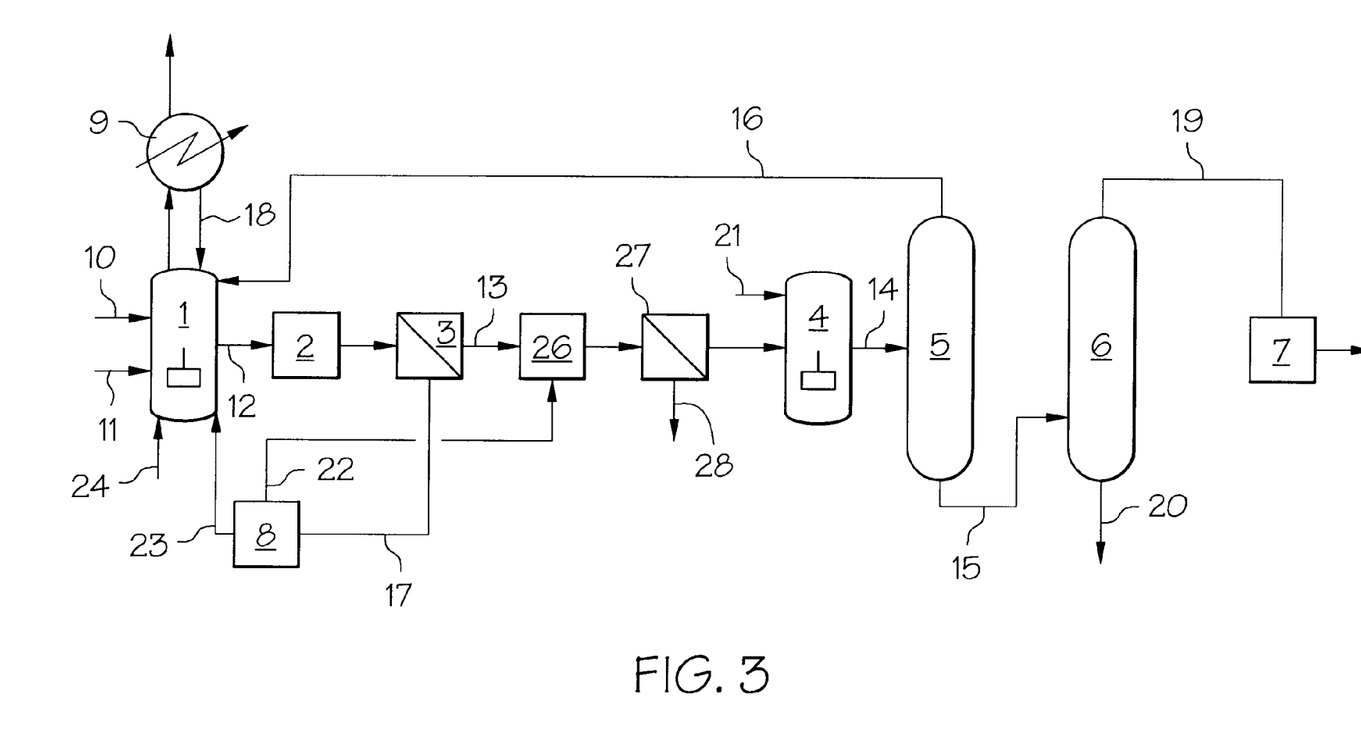
FIG. 3 is a flow sheet similar to FIG. 2 of a process in accordance with a further example of the invention.

Another embodiment of the invention is shown in FIG. 3, in which the same numerals indicate the same components as the embodiment of FIG. 2. In particular, it will be seen that in the FIG. 3 embodiment the naphthalenedicarboxylic acid crystals produced in separator 3 are fed to slurry vessel 26 where the crystals are washed with hot water, optionally containing acetic acid, to remove trimellitic acid residues prior to esterification. By removing trimellitic acid residues prior to esterification this option simplifies purification and facilitates recycle of byproducts. The source of first wash liquids can be the condensed overhead stream 22 from the separation tower 8 or the condensed reflux 18 from oxidation reactor 1. The washed acid is separated in a further solid/liquid separator 27 and conveyed to the estserification reactor 4. Alternatively, the two steps of separation (separators 3 and 27) may be accomplished on a single belt or rotary vacuum filter.

Figure 4:
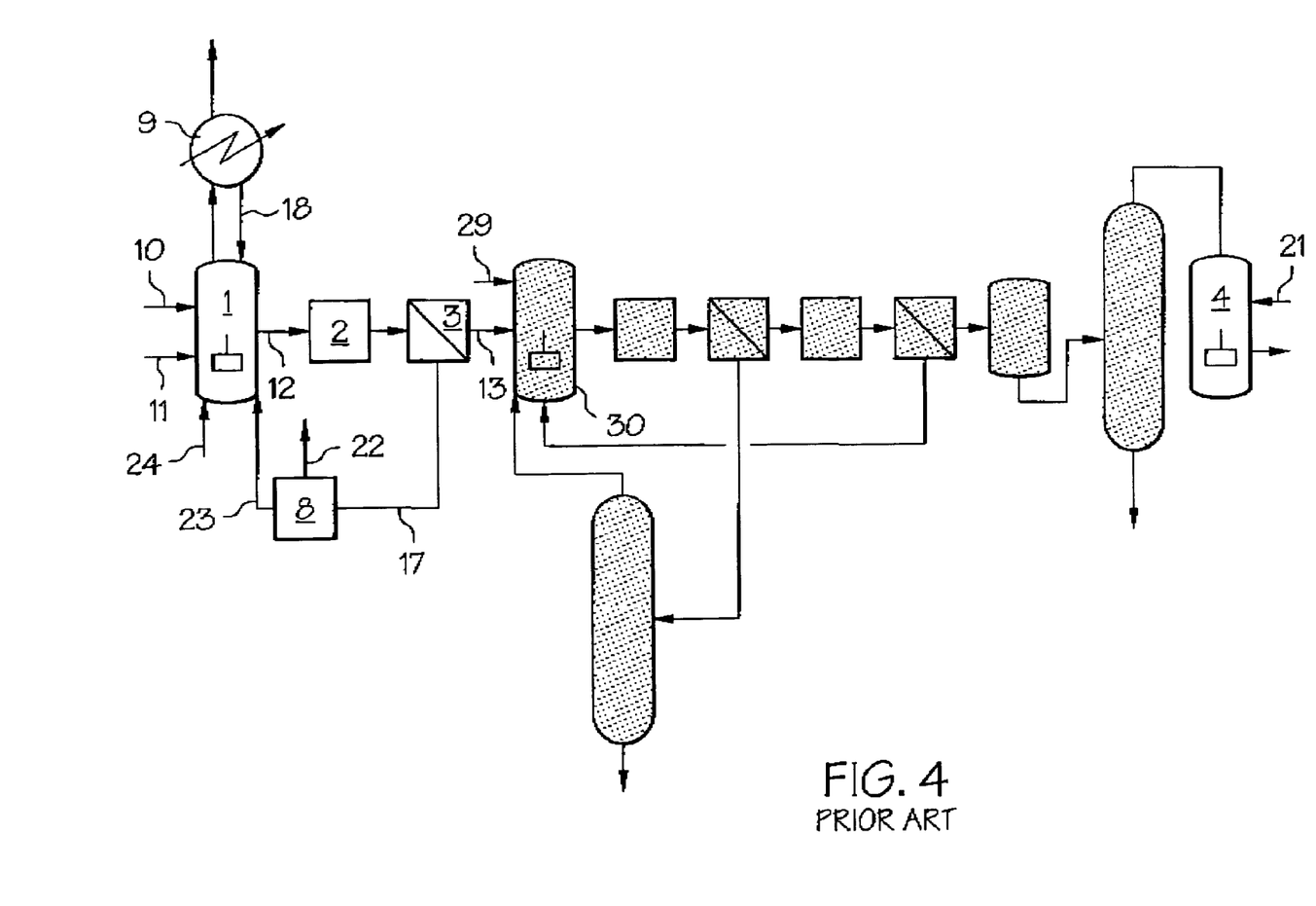
FIG. 4 is a flow sheet of a prior art process.

For comparison, a prior art process for producing PEN is shown in FIG. 4, in which again the same numerals indicate the same components as the embodiment of FIG. 2. In particular, it will be seen that in the prior art embodiment, additional steps (shown shaded) are required after the preparation and separation of crude naphthalene dicarboxylic acid (stream 13) and before the glycol esterification reactor 4. These steps include the preparation of the dimethyl ester of 2,6-naphthalenedicarboxylic in a further esterification reactor 30 by the addition of methanol (stream 29) and the subsequent purification of the dimethyl ester by crystallization and distillation acid prior to transesterification to the glycol ester in the reactor 4. The prior art process also has an additional disadvantage in that the methanol from the transesterification reactor 4 must be recovered and recycled.

The various steps in the process of the invention will now be described in more detail.

Oxidation of 2,6-Dialkylnaphthalenes to 2,6-Naphthalenedicarboxylic Acid

In the first stage of the process of the invention, crude 2,6-naphthalenedicarboxylic acid is prepared by oxidizing 2,6-dialkylnaphthalenes in the liquid phase with molecular oxygen in the presence of a transition metal catalyst and an oxidation promoter. Preferably, the oxidation promoter comprises volatile partial oxidation esterified intermediates recycled from the purification stage of the process as described below.

The oxidation reaction is a liquid phase reaction wherein a catalyst comprising one or more variable-valency transition metals, such as cobalt and manganese, and oxidation promoter components are used to catalyze the oxidation of the alkyl substituents on 2,6-dialkylnaphthalene to carboxylic acid substituents. A gas containing molecular oxygen supplies the oxygen for the oxidation reaction, and water and carbon oxides are also produced. The reaction is typically and preferably conducted in a continuous manner wherein the reaction components comprising the 2,6-dialkylnaphthalene feedstock, catalyst components, oxidation promoters, source of molecular oxygen, and solvent are continuously added to selected sites in an oxidation reaction zone under predetermined reaction conditions and addition rates. In a continuous oxidation process, a reaction product mixture containing the desired 2,6-naphthalenedicarboxylic acid is typically continuously removed from the reaction zone.

During the start-up of a continuous oxidation process, the composition of the reaction mixture in the oxidation reaction zone changes as the reaction proceeds. However, after a period of time, steady state conditions are achieved and the composition of the reaction mixture in the reaction zone becomes constant, i.e., so-called "lined-out" conditions are obtained. Due to its insolubility, most of the 2,6-naphthalenedicarboxylic acid product is typically in solid form in the reaction mixture, in the form of a slurry, and can be separated from the liquid part of the reaction product mixture, the so-called oxidation reaction mother liquor, by any suitable method for partitioning solids from liquids.

Prior to separating the mother liquor from 2,6-naphthalenedicarboxylic acid, the reaction mixture slurry is preferably cooled in one or more crystallizer vessels, preferably arranged in series, to crystallize 2,6-naphthalenedicarboxylic acid dissolved in the oxidation reaction mother liquor thereby maximizing recovery of the desired 2,6-naphthalenedicarboxylic acid, and also reducing the temperature of the oxidation reaction mixture so the 2,6-naphthalenedicarboxylic acid contained therein can be separated using conventional separation equipment.

The preferred hydrocarbon feedstock for the continuous oxidation process of this invention is 2,6-dimethylnaphthalene. Conveniently, the source of 2,6-dimethylnaphthalene is from one or more of the synthetic processes known for preparing 2,6-dimethylnaphthalene. One such route starts with o-xylene and butadiene wherein the o-xylene is alkenylated in the liquid phase with butadiene in the presence of an alkali metal catalyst such as sodium and/or potassium to form 5-ortho-tolyl pentene. Such an alkenylation reaction is disclosed in U.S. Pat. No. 3,953,535. The 5-ortho-tolyl pentene is subsequently cyclized to form 1,5-dimethyltetralin, which is then dehydrogenated to form 1,5-dimethylnaphthalene. The 1,5-dimethylnaphthalene is isomerized to form 2,6-dimethylnaphthalene which can be isolated as a solid product. A suitable procedure for conducting these cyclization, dehydrogenation and isomerization reactions is disclosed in U.S. Pat. No. 4,950,825. Another process for preparing 2,6-dimethylnaphthalene starting from m-xylene, propylene and carbon monoxide is disclosed in U.S. Pat. No. 5,023,390. These processes are complex and the product still requires purification by crystallization technologies and while any process for preparing or isolating 2,6-dimethylnaphthalene is suitable as a source of the 2,6-dimethylnaphthalene used in the process of this invention the preferred route is one that provides the material at the lowest cost.

Within a refinery 2,6-dimethylnaphthalene feedstock can be isolated from naphthalene-containing refinery streams including so-called tar fractions, or from one or more of the various bottoms fractions produced during crude oil refining processes. However, the concentration of 2,6-dimethylnaphthalene in these refinery streams is generally low and it is therefore difficult to obtain suitably large quantities of the desired 2,6-dimethylnaphthalene feedstock from such streams. However, a process has been developed wherein fractions of light cycle oil and heavy reformate are separated, isomerized and alkylated to provide a suitable source of dimethylnaphthalenes. Such a process is described in, for example, U.S. Pat. No. 6,121,501.

Preferably, the 2,6-dimethylnaphthalene used as the feed to the oxidation process of this invention is at least about 97.5 wt %, and more preferably at least about 99 wt %, pure.

The source of molecular oxygen employed in the liquid phase oxidation process of this invention can vary from pure oxygen to a gas containing about 0.1 percent by weight molecular oxygen, with the remaining gas being a ballast gas, such as nitrogen, that is inert in the liquid phase oxidation. Most preferably, for reasons of economy, the source of molecular oxygen is air. In order to avoid the formation of explosive mixtures, the molecular oxygen-containing gas introduced into the reaction zone should be added in an amount such that the exhaust gas mixture exiting the reaction zone contains from about 0.5 to 8% by volume oxygen measured on a solvent-free basis.

The solvent used for the liquid phase oxidation reaction comprises a low molecular weight aliphatic carboxylic acid having 1 to 6 carbon atoms, a mixture of two or more of such low molecular weight carboxylic acids, or a mixture of one or more of such low molecular weight carboxylic acids with water, for example, about 1 to about 15 wt % water. Suitable solvents include, for example, acetic acid, propionic acid, n-butyric acid and mixtures of one or more of these acids with water. Preferably, due primarily to cost and availability, the oxidation solvent added to the reaction mixture comprises acetic acid containing water, preferably about 3 to 10 wt % water. Additionally, water is formed as a product of the oxidation reaction.

The oxidation reaction is an exothermic reaction and the heat generated is dissipated in part by the vaporization of the oxidation reaction solvent. Typically, a portion of the vaporized solvent or overhead is withdrawn from the reaction zone, cooled to condense the vapor, and the resulting condensate is returned to the oxidation reaction mixture. This vapor is a mixture of water and, when acetic acid is used as the aliphatic monocarboxylic acid solvent, acetic acid. By separating the water from the acetic acid before the condensate is returned to the reaction zone, the water level in the reaction zone can be adjusted to levels lower than that which would otherwise develop in the reaction zone due to the formation of water during the oxidation reaction. However rather than separating the water from the acetic acid present in the condensed vapor, it is possible to use such condensed stream to dilute the oxidation reaction slurry after the slurry is withdrawn from the oxidation reaction zone or use the condensate in one or more of the crystallizers used to dilute and cool the slurry mixture containing 2,6-naphthalenedicarboxylic acid after the slurry is withdrawn from the oxidation reaction zone. The addition of such condensed stream, which contains acetic acid and water, to the oxidation reaction slurry provides for a purer 2,6-naphthalenedicarboxylic acid after the 2,6-naphthalenedicarboxylic acid is separated from the diluted oxidation reaction mother liquor. In particular, it serves to reduce the levels of catalyst metals and trimellitic acid in the 2,6-naphthalenedicarboxylic acid product. After separating the 2,6-naphthalenedicarboxylic acid from the mother liquor which preferably has been diluted with the aforementioned condensed stream, the mother liquor can be treated, typically by distillation, to recover acetic acid for recycle to the oxidation reaction mixture. A portion of the mother liquor comprising the transition metals can also be recycled to the oxidation reaction mixture.

The weight ratio of aliphatic monocarboxylic acid solvent to 2,6-dimethylnaphthalene for the liquid phase oxidation reaction, i.e., the solvent ratio, is suitably in the range of about 2:1 to about 12:1, preferably in the range of about 3:1 to about 6:1, respectively. Low ratios of monocarboxylic acid solvent to 2,6-dimethylnaphthalene, i.e. 2:1 to 6:1, are advantageous because greater amounts of 2,6-naphthalenedicarboxylic acid can be produced per reactor volume. The solvent ratio, as used herein, means the amount of solvent, by weight, in the oxidation reaction slurry withdrawn from the reaction zone divided by the amount, by weight, of 2,6-dimethylnaphthalene added to the oxidation reaction zone.

The catalyst employed in the liquid phase oxidation according to the process of this invention comprises heavy metals or mixtures of heavy metals, such as those taught in U.S. Pat. No. 2,833,816 (manganese, cobalt, chromium, vanadium, molybdenum, tungsten, tin, or cerium). U.S. Pat. No. 3,299,125 expanded this list of variable-valency metals to further include copper, iron, lead, nickel, selenium, silver or zinc in conjunction with scandium, zirconium lanthanum, and hafnium. Both of these patents are herein incorporated by reference. Other publications indicate that higher transition metals such as samarium also act as oxidation catalysts; however the most commonly used systems are based on cobalt and manganese. Each of the cobalt and manganese components can be provided in any of its known ionic or combined forms that provides for soluble forms of cobalt and manganese in the oxidation reaction solvent. For example, one or more of cobalt and/or manganese acetate tetrahydrate, carbonate can be employed.

The oxidation promoter used in the oxidation step of the process of the invention can be a halogen-containing compound, preferably a bromine-containing compound. Suitable sources of bromine include elemental bromine, i.e. $Br_2$, ionic bromides such as HBr, NaBr, KBr, and $NH_4Br$, etc., and organic bromides which are known to provide bromide ions at the operating temperature of the oxidation such as, for example, benzyl bromide, mono- and dibromoacetic acid, bromoacetyl bromide, tetrabromoethane and ethylene dibromide. Alternatively, the oxidation promoter can be an organic species such as acetaldehyde and methylethylketone.

According to one embodiment of the invention, it has been found that the oxidation promoter can be a non-bromine based organic species produced as a by-product of the oxidation process and separated during the purification of the crude acid described in detail below. Thus the volatile 6-formyl-2-naphthalene carboxylate and 6-methyl-2-naphthalene carboxylate glycol esters formed as by-products in the oxidation step have been found to act as oxidation promoters. By recycling these by-products to the oxidation step it may be possible to develop a bromine free oxidation process. Such an oxidation process would be less corrosive than those employing bromine and would allow the oxidation to occur in equipment constructed of lower cost alloys.

The individual catalyst components used for the oxidation process can be introduced into the reaction zone where the liquid phase oxidation is occurring either separately or in one or more combinations, and they can be introduced in any convenient manner, for example, as a solution in water or a mixture of water and the monocarboxylic acid or other suitable solvent.

In the process of this invention it is advantageous to remove solvent from the oxidation reaction mixture by removing at least a portion of the condensed overhead, rather than returning all of the condensed overhead vapor or condensate to the oxidation reaction mixture. As discussed hereinabove, it is advantageous to use the condensed overhead to dilute the oxidation product slurry exiting the oxidation reaction zone. The amount of such solvent removed is preferably an amount which provides for a concentration of transition metal catalyst in the reaction mixture, calculated as elemental metals, of at least about 0.10 weight percent, preferably at least about 0.20 weight percent, and more preferably at least about 0.30 weight percent based on the weight of the solvent in the reaction zone. As discussed hereinabove, removal of the overhead condensate also serves to achieve the desired low levels of water in the oxidation reaction mixture.

The reaction temperature for the liquid phase oxidation according to the process of this invention is suitably in the range of about 350 to about 420° F., and preferably in the range of about 375 to about 415° F. Reaction temperatures higher than about 420° F. or lower than about 350° F. generally cause reduced yields of the desired 2,6-naphthalenedicarboxylic acid.

The apparatus used to conduct the oxidation reaction can be a tank reactor (preferably stirred), a plug flow reactor, a compartmented reactor or a combination of two or more of these reactors. For example, the apparatus can consist of two or three stirred tank reactors arranged in series. Optionally, a plug flow reactor can suitably be used to mix and pre-heat the reactants before they enter the stirred tank reactor or reactors.

In operation, the minimum pressure at which the oxidation reaction is maintained is preferably a pressure which will maintain at least 50 weight percent and more preferably at least 70 weight percent of the solvent in the oxidation reaction zone in the liquid phase. When the solvent is a mixture of acetic acid and water, suitable reaction pressures are from about 0.1 atmosphere absolute to about 35 atmospheres absolute, and typically in the range of about 10 atmospheres absolute to about 30 atmospheres absolute.

During the oxidation reaction of this invention, 2,6-dimethylnaphthalene can be added to the oxidation reaction zone at various rates. The rate at which the 2,6-dimethylnaphthalene is added is related to the solvent ratio and the reactor residence time. The reactor residence time in minutes is the oxidation reactor drain weight in pounds divided by the reaction mixture effluent rate in pounds per minute. The solvent ratio and residence time are related to a value termed "hydrocarbon throughput" or HCTP. HCTP, as used herein, is lb moles (a mass unit of moles in lbs) of 2,6-dimethylnaphthalene added per cubic foot of reaction solvent in the reactor per hour, and is a measure of productivity for the oxidation reactor.

The oxidation reaction mixture produced in the reaction zone during the liquid phase oxidation reaction is removed, preferably continuously, from the reaction zone typically in the form of a slurry of solid 2,6-naphthalenedicarboxylic acid in the reaction mixture mother liquor. The mother liquor typically comprises the low molecular weight monocarboxylic acid solvent, water, dissolved impurities and catalyst components. The desired 2,6-naphthalenedicarboxylic acid is separated from the mother liquor by one or more suitable methods for partitioning a solid from a liquid phase such as, for example, centrifugation, filtration, settling, etc. As discussed hereinabove, prior to this partitioning step, the oxidation reaction mixture can be cooled. The cooling can be accomplished by any convenient method, for example, a tube and shell-type heat exchanger can be used, or the reaction mixture can be cooled in a vessel equipped with cooling coils or a cooled reactor jacket. Alternatively, the reaction mixture can be added to a vessel at a pressure lower than that used for the oxidation reaction. At the reduced pressure the oxidation reaction solvent boils thereby cooling the reaction mixture. An overhead condenser can be used to cool, condense and return the overhead vapor to the vessel to further assist in the cooling. Two or more of these vessels can be used in series, each at a temperature somewhat lower than the previous vessel, to cool the reaction mixture in a stepwise manner. The oxidation reaction mixture is typically cooled to about 250° F. or below prior to partition the 2,6-naphthalenedicarboxylic acid from the oxidation reaction mother liquor.

After the oxidation reaction mixture exits the oxidation reaction zone, but prior to the partitioning of the 2,6-naphthalenedicarboxylic acid from the mother liquor, the reaction product mixture can be contacted with an oxygen-containing gas in the absence of freshly added 2,6-dimethylnaphthalene. This treatment serves to oxidize some of the 6-formyl-2-naphthalene carboxylate formed as a by-product of the oxidation process. The treatment can be conducted at any time after the reaction mixture exits the oxidation reaction zone, but is preferably conducted as the mixture exits the oxidation reaction zone. The treatment can be effected in one or more suitable reactor vessels, such as a tank reactor or a compartmented reactor, but preferably a tank reactor is used, with the oxygen-containing gas being sparged into the reactor, preferably at a point adjacent the bottom of the reactor. The further oxidation step can be conducted at a temperature in the range of about 150 to about 450° F. and preferably in the range of about 350 to about 450° F. Although the rate of introduction of oxygen-containing gas is not critical, there should be sufficient molecular oxygen present to oxidize the formyl group on the 6-formyl-2-naphthalene carboxylate within a residence time of about 0.25 hour to about 2 hours at the temperature used. As described hereinabove, the vent gas composition must be controlled to prevent the formation of explosive mixtures. It is also possible to treat the reaction mixture with the oxygen-containing gas when the oxidation reaction mixture is being cooled, as described above. Thus, for example, while the reaction mixture is held at reduced pressure to provide for the cooling of the reaction mixture, the oxygen-containing gas can be sparged through the reaction mixture. The oxygen-containing gas can contain from about 0.1 wt % molecular oxygen to pure oxygen, with the remaining gas being an inert ballast gas, such as nitrogen.

In one embodiment of the present invention water and preferably water and acetic acid (or other low molecular weight aliphatic carboxylic acid) is added to the effluent from the oxidation reaction zone in order to increase the solubility of the oxidation catalyst metals, trimellitic acid, and the products that are formed by complexing of trimellitic acid with the cobalt and manganese oxidation catalyst metals. If the optional treatment with oxygen-containing gas is used, the addition of water or combination of water and acetic acid can occur either prior to or after the treatment with the oxygen-containing gas. The addition of acetic acid and water decreases the amount of metals and trimellitic acid that would otherwise be incorporated in the 2,6-naphthalenedicarboxylic acid when it is partitioned, in the manner described hereinabove, from the mother liquor.

The amount of acetic acid (or other low molecular weight aliphatic carboxylic acid) and water added to the effluent slurry from the oxidation reaction zone is conveniently from about 1 to about 200 wt %, preferably about 20 to about 150 wt %, and most preferably about 50 to about 100 wt %, of the slurry. The weight ratio of acetic acid to water added to the effluent slurry is suitably about 0.1:1 to about 10:1, more preferably about 0.2:1 to about 7:1. As described hereinabove, a preferred source of water and acetic acid for adding to the oxidation reaction effluent slurry is the mixture of acetic acid and water resulting from the condensation of the overhead vapors from the liquid phase oxidation reaction. The source of acetic acid and water can also be obtained from a scrubber or absorber used to remove acetic acid from that part of the oxidation reactor overheads which is not condensed in the overhead condenser. In this scrubber or absorber, water is used to remove or scrub the acetic acid from the gaseous, non-condensed oxidation reactor overheads. Although other sources of water, such as deionized water, and other sources of acetic acid, such as fresh acetic acid, can be added to the slurry exiting the oxidation reactor, it is advantageous to use the water and acetic acid from the absorber or from the condensed oxidation reactor overhead because such a procedure does not require the use of sources of solvent from outside the process and also because it does not add additional water to the process which must be separated from acetic acid in order to be able to reuse the valuable acetic acid. The acetic acid and water is preferably added continuously to the effluent slurry.

In another embodiment, the crude 2,6-naphthalenedicarboxylic acid, after its separation from the reaction mixture mother liquor, can be redispersed or reslurried in a suitable solvent such as water, a low molecular weight carboxylic acid or a mixture of water and a low molecular weight carboxylic acid at a weight ratio of about 0.1 to about 1 part of 2,6-naphthalenedicarboxylic acid per part of solvent. Preferably, at least a portion of the solvent used to redisperse or reslurry the 2,6-naphthalenedicarboxylic acid in this manner is the condensate from the overhead of the oxidation reaction mixture. After this reslurry step, the 2,6-naphthalenedicarboxylic acid can be separated from the solvent in the manner described hereinabove. The reslurry step provides for a purer 2,6-naphthalenedicarboxylic acid. The separated solvent comprising water and acetic acid can, for example, be returned, at least in part, to the oxidation reactor or it can, at least in part, be distilled to recover acetic acid for recycle to the oxidation reactor.

Mother liquor that is separated from the oxidation reaction mixture contains most of the oxidation metal catalyst components. However, the mother liquor also contains undesirable reaction side products such as trimellitic acid which is preferentially soluble in hot aqueous solutions. Nevertheless, this mother liquor is valuable because it can be recycled, either prior to or after dilution as described hereinabove, to the oxidation reaction zone as a source of acetic acid and, more importantly, as a source of active catalyst metals. The mother liquor can be recycled to the oxidation reacting zone in an amount in the range of about 1 weight percent of the mother liquor to about 100 weight percent. Preferably, about 5 to about 50 weight percent of the mother liquor is recycled, the remaining portion typically being treated to recover the acetic acid and catalyst metals for recycle to the oxidation reaction mixture.

A preferred method for recycling the valuable catalyst metals to the oxidation reaction zone comprises removing the metals from the mother liquor using processes known to those of skill in the art, such as carbonate precipitation, oxalate precipitation, or by ion exchange processes such as that disclosed in U.S. Pat. No. 4,162,991. Additionally, the mother liquor can be concentrated to recover acetic acid solvent and the residue containing oxidation catalyst metals can be incinerated. Cobalt and manganese catalyst metals from the resulting ash can be recycled to the reaction mixture.

Purification of the Crude 2,6-Naphthalenedicarboxylic Acid

After its separation from the oxidation mother liquor, the solid, crude naphthalene dicarboxylic acid is washed, and optionally dried. The resultant acid is then esterified with an alcohol in the liquid phase to give a solution of naphthalenedicarboxylic acid ester(s). The catalyst employed for this esterification comprises residual transition metals from the oxidation reaction, or optionally comprises added transition metal compounds. By the esterification reaction, a naphthalenedicarboxylic acid monoester and a naphthalenedicarboxylic acid diester, each of which is an ester of the naphthalenedicarboxylic acid, are produced, and these esters are dissolved in the alcohol, normally in aqueous solution.

The alcohol used in the esterification reaction may be pure or may comprise an aqueous alcohol mixture. The alcohol used is preferably an alcohol having 8 or less carbon atoms, and more preferably is an aliphatic dihydric alcohol, such as ethylene glycol, 1,3-propane diol and 1,4-butane diol. Most preferably, the alcohol is ethylene glycol and is used as an aqueous solution containing 20 to 100 wt %, preferably 40 to 90 wt %, more preferably 60 to 80 wt %, ethylene glycol based on 100% by weight of the total of water and ethylene glycol.

The esterification of the naphthalenedicarboxylic acid is carried out under a pressure of usually 2 to 80 kg/cm$^2$, preferably 10 to 50 kg/cm$^2$, at a temperature of usually 200 to 300° C., preferably 160 to 280° C., for a period of usually 0.2 to 6 hours, preferably 1 to 4 hours. Water may be removed from the esterification reaction.

After the esterification reaction, volatile impurities contained in the crude naphthalenedicarboxylic acid, such as mono-aldehydes, are removed by distillation. The boiling point of 6-formyl-2-naphthalene carboxylate ester (FNA-EG) is considerably lower than that the boiling points of naphthalene dicarboxylic acid monoester (NDA-1EG) and naphthalenedicarboxylic acid diester (NDA-2EG). Using a Pro II simulation model, the boiling point of the ethylene glycol ester of 6-formyl-2-naphthalene carboxylic acid has been determined to be 247.2° C., whereas that of the diglycol ester of 2,6-naphthalenedicarboxylic acid has been determined to be 462.8° C., a difference of approximately 215° C. The glycol esters of trimellitic acid are much higher boiling, 731.7° C., and would remain as heavies if the diglycol ester of 2,6-naphthalenedicarboxylic acid is optionally distilled.

To examine the practicality of separating the components by distillation, the vapor pressure curves for the components were estimated. First, based on the Pro II estimates of NBP, the heats of vaporization ($Hv_n$) were estimated using Kistiakowsky's equation:

$$Hv_n/T_n=8.75+1.987T_n$$

where $T_n$=NBP in ° K, and H=cal/g mole.

Using Hv from the above equation vapor pressure curves were computed using the Clausius Clapeyron equation:

$$\ln(P_2/P_1)=-H/R(1/T_2-1/T_1)$$

where $T_1$ and $T_2$ are expressed in ° K, with $T_1$=NBP in ° K and $P_1$=760 torr.

Figure 1:
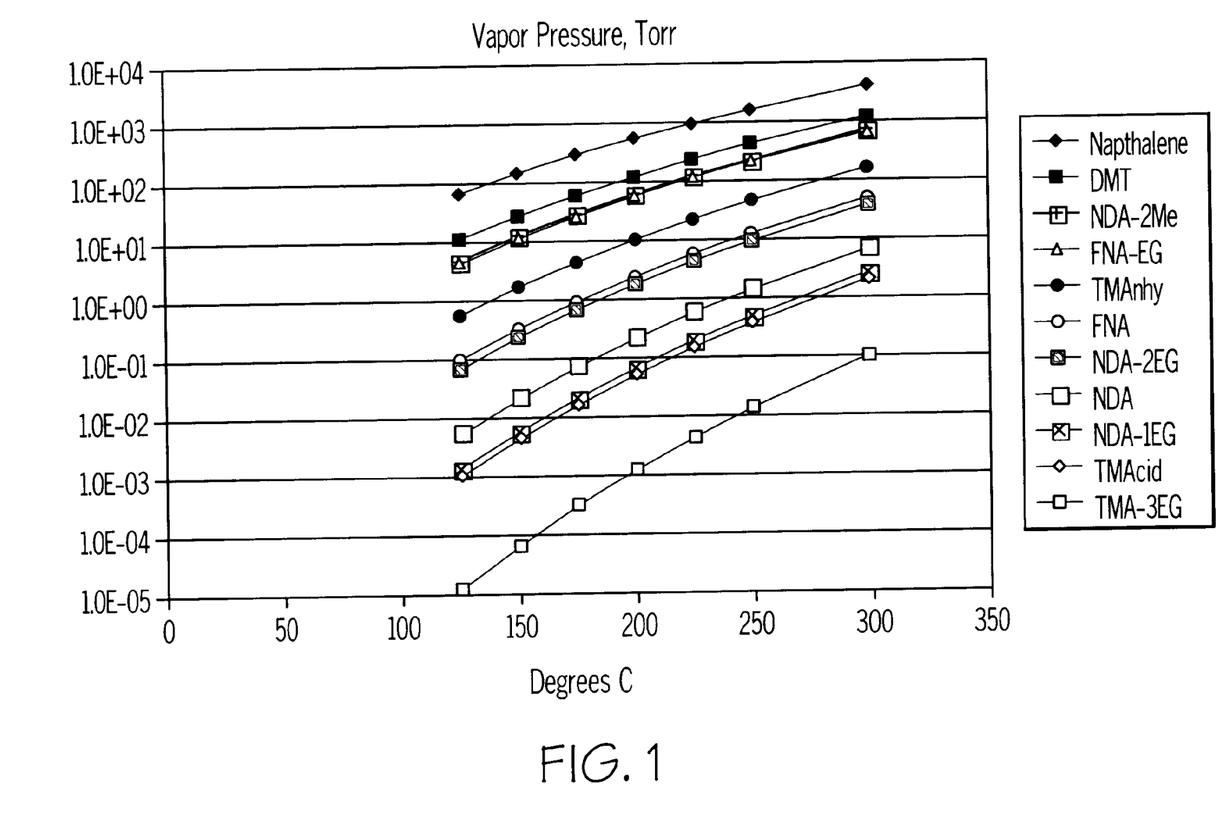
FIG. 1 is a graph showing the estimated vapor pressure curves for the bis-glycol esters of 2,6-naphthalene dicarboxylic acid and various possible impurity compounds produced during the oxidation/esterification process of the invention.

The results are shown in FIG. 1. The upper lines indicate compounds boiling at lower temperatures than the diester of naphthalenedicarboxylic acid with ethylene glycol, bis (2-hydroxyethyl)-2,6-naphthalenedicarboxylate (NDA-2EG), and the lower lines indicate compounds boiling at higher temperatures than NDA-2EG. Curves for naphthalene, the methyl diester of 2,6- naphthalenedicarboxylic acid (NDA-2Me) and dimethylterephthalate (DMT) are included for reference. Other vapor pressure curves given in FIG. 1 are those for 2'-hydroxyethyl-2-formyl-6-naphthoate (FNA-EG), trimellitic anhydride (TMAnhy), 2-formyl-6-naphthoic acid (FNA), 2,6-naphthalenedicarboxylic acid (NDA), 2-hydroxyethyl-2,6-naphthalenedicarboxylate (NDA-1EG), trimellitic acid (TMAcid) and tris (2-hydroxyethyl)-trimellitate (TMA-3EG).

The estimated vapor pressure curves shown in FIG. 1 indicate that the light and heavy impurities can readily be separated from the diglycol ester of NDA by distillation. The exception is any remaining non-esterified 2-formyl-6-naphthoic acid (FNA), which would boil close to NDA-2EG. Such a potential problem indicates that the esterification reaction should be run to a high degree of conversion of the acid functionality to the ester functionality.

It will be seen from FIG. 1 that distillation of the esterification product will remove the 2'-hydroxyethyl-2-formyl-6-naphthoate (FNA-EG) and the dimethyl-2,6-naphthalenedicarboxylate (NDA-2Me) as volatile impurities whereas, in accordance with the invention, it has been found that these esters can be recycled to the oxidation reaction to act as oxidation promoters. Thus in one embodiment of the invention the total effluent from the esterification of the crude solid product from the oxidation reaction is distilled with recycle of the volatile impurities to the oxidation reactor as promoters. This embodiment is shown in FIG. 2. The pure distilled naphthalenedicarboxylic acid diester can be directly fed to a polyesterification step, or crystallized and stored to provide for a disengagement of the oxidation, esterification and purification steps from the polyesterification step. Such disengagement will additionally allow for the preparation of a range of mixed copolyesters for diverse markets.

In another embodiment of the invention, the volatile components are removed by flash distillation, whereafter the resulting solution is cooled, optionally after the addition of further ethylene glycol, to crystallize (precipitate) the naphthalenedicarboxylic acid diester and any naphthalenedicarboxylic acid monoester. The precipitated naphthalenedicarboxylic acid esters are separated from the alcohol solution to obtain a mixture of the naphthalenedicarboxylic acid esters containing small amounts of impurities, usually not more than 100 ppm, preferably not more than 50 ppm. The ratio between the naphthalenedicarboxylic acid monoester and the naphthalenedicarboxylic acid diester obtained in this embodiment can be controlled by adjusting the alcohol concentration of the alcohol aqueous solution and/or the temperature for the crystallization. In addition, the mono- to diester ratio can be controlled by adjusting the time or temperature of the esterification reaction A further embodiment is shown in FIG. 3, wherein the crude solid product from the oxidation reactor is sufficiently washed with hot water, optionally initially containing acetic acid to remove trimellitic acid residues prior to esterification. The source of the initial wash liquid can be the condensed overhead stream from the acetic acid/water separation tower or the condensed reflux from the oxidation reactor.

These methods of purifying crude naphthalenedicarboxylic acid according to the present invention are very suitable for obtaining a mixture of naphthalenedicarboxylic acid mono-ester and naphthalene dicarboxylic acid diester having a low content of 6-formyl-2-naphthalene carboxylate and 6-methyl-2-naphthalene carboxylate from crude naphthalene dicarboxylic acid. In particular, the concentration of aldehydes in the ester mixture is usually not more than 1,000 ppm, preferably not more than 500 ppm. The high-purity naphthalene dicarboxylate esters produced are suitable for use as starting materials for preparing PEN or can be mixed with other dicarboxylic acids, or dicarboxylic acid esters for the preparation of mixed polyesters comprising a naphthalene dicarboxylic acid residue. If ethylene glycol is used as the alcohol in the above method and if the resulting mixture of the high-purity naphthalenedicarboxylic acid monoester and the naphthalene dicarboxylic acid diglycolester is subjected to polycondensation reaction, optionally adding ethylene glycol to the mixture, polyethylene naphthalate having a low impurity content can be obtained.

By using excess alcohol, it is possible to produce essentially only the diester in the esterification reaction. After removal of the volatile impurities, the pure diester can be directly used in polyesterification reactions.

High-purity naphthalenedicarboxylic acid can be obtained using the process of the invention by lowering the alcohol concentration of the aqueous alcoholic solution remaining after flash distillation of the partial oxidation products. As a result, the naphthalene carboxylic acid ester(s) is hydrolyzed to produce the acid, which precipitates and hence can be recovered.

Production of Polyethylene Naphthalate

The high purity naphthalenedicarboxylic acid and/or acid diester produced in accordance with the process described above can be converted to polyethylene naphthalate by a conventional polycondensation reaction. Such a reaction typically involves heating the mixture to a temperature of not lower than the melting point of the desired polyethylene naphthalate under reduced pressure in the presence of a polycondensation catalyst, while glycol eliminated during the reaction is distilled from the system. Additional ethylene glycol may be added to the mixture if required.

The polycondensation reaction is conveniently carried out at a temperature of 250 to 290° C., preferably 260 to 280° C., and a pressure of not more than 500 Torr, preferably not more than 200 Torr.

Examples of the polycondensation catalysts which can be employed herein include germanium compounds, such as germanium dioxide, germanium tetraethoxide and germanium tetra-n-butoxide; antimony catalysts, such as antimony trioxide; and titanium compounds, such as titanium tetrabutoxide. The polycondensation catalyst is conveniently used in an amount sufficient to provide 0.0005 to 0.2% wt, preferably 0.001 to 0.05% wt, of the catalytic metal based on the total weight of the naphthalene dicarboxylic acid ester and ethylene glycol.

The polyethylene naphthalate prepared by the polycondensation reaction has an intrinsic viscosity, as measured in o-chlorophenol at 25° C., of usually 0.4 to 1.5 dl/g, and has a density of usually not less than 1.37 g/cm$^3$.

The polyethylene naphthalate obtained as above may be further subjected to solid phase condensation to produce a PEN resin having excellent oxygen barrier properties and transparency. This is typically effected by controlling the rate of heating and the temperature so as to build up sufficient crystallinity to avoid particle agglomeration during the solid phase condensation step. For example, the polyethylene naphthalate can be subjected to a precrystallization step wherein it is maintained in a dry state at a temperature of not lower than the temperature at which crystallization occurs (during the initial heating of an amorphous sample in a differential scanning calorimeter) and lower than its melting point, preferably at a temperature of higher than the temperature at which crystallization occurs (during the initial heating of an amorphous sample in a differential scanning calorimeter) by not less than 10° C. and lower than its melting point by not less than 40° C. for a period of 1 to 30 minutes, preferably 5 to 20 minutes; and a step of solid phase polycondensation wherein the polyethylene naphthalate is heated at a temperature of usually 190 to 230° C., preferably 195 to 225° C., under a pressure of usually 1 kg/cm$^2$ g to 10 Torr, preferably atmospheric pressure to 100 Torr. Another approach to solid phase polycondensation is to hold the crystallized polyethylene naphthalate a temperature of 190 to 230° C., preferably 195 to 225° C., for several hours under a nitrogen sweep.

The polyethylene naphthalate obtained as above has a low impurity content and has good transparency and good oxygen barrier properties when fabricated into a container or into a thin film.

We claim:

1. A process for making a purified aryldicarboxylic acid by esterification, comprising the steps of:
   (i) oxidizing a disubstituted aryl hydrocarbon to form a mixture which comprises a crude aryldicarboxylic acid having impurities;
   (ii) separating the crude aryldicarboxylic acid having impurities from the mixture;
   (iii) reacting the crude aryldicarboxylic acid having impurities with an alcohol to esterify at least a portion of the crude aryldicarboxylic acid and the impurities to produce an esterification effluent containing an aryldicarboxylic acid ester and volatile esterified impurities;
   (iv) removing the volatile esterified impurities;
   (v) separating a purified aryldicarboxylic acid ester from the esterification effluent; and
   wherein at least a portion of the volatile esterified impurities removed in step (iv) is recycled to step i) to act as an oxidation promoter.

2. The process of claim 1 wherein the volatile esterified impurities are the sole oxidation promoter.

3. The process of claim 1 wherein the recycled volatile esterified impurities comprise aldehyde esters.

4. The process of claim 1 wherein the oxidizing step (i) includes oxidizing the disubstituted aryl hydrocarbon in the presence of a metal catalyst.

5. The process of claim 4 wherein the metal catalyst is selected from the group consisting of manganese, cobalt, chromium, vanadium, molybdenum, tungsten, tin, and cerium.

6. The process of claim 1 wherein the disubstituted aryl hydrocarbon of step (i) is selected from the group consisting of a xylene, a dimethylnaphthalene and mixtures thereof.

7. The process of claim 6 wherein the disubstituted aryl hydrocarbon is p-xylene or 2,6-dimethylnaphthalene.

8. The process of claim 1 wherein the crude aryldicarboxylic acid of step (i) comprises a dicarboxylic acid selected from the group consisting of terephthalic acid, naphthalene dicarboxylic acid and mixtures thereof.

9. The process of claim 1 wherein the separating step (v) includes separating the purified aryldicarboxylic acid ester from the esterification effluent by crystallization or distillation.

10. The process of claim 1 wherein the removing step (iv) includes removing the volatile esterified impurities by distillation.

11. A process for making a purified naphthalene dicarboxylic acid by esterification, comprising the steps of:
    (i) oxidizing at least a portion of 2,6-dimethylnaphthalene to produce an oxidation effluent which comprises crude naphthalene dicarboxylic acid having impurities;
    (ii) separating the crude naphthalene dicarboxylic acid having impurities from the oxidation effluent;
    (iii) optionally washing the separated crude naphthalene dicarboxylic acid having impurities with aqueous acetic acid;
    (iv) mixing the separated crude naphthalene dicarboxylic acid having impurities with an aqueous solution of ethylene glycol to form a mixture;
    (v) heating the resulting mixture to esterify at least a portion of the naphthalene dicarboxylic acid and the impurities to produce a naphthalene dicarboxylic acid ester and volatile esterified impurities in an aqueous glycol solution;
    (vi) removing the volatile esterified impurities from the aqueous glycol solution; and
    (vii) separating a purified naphthalene dicarboxylic acid ester from the aqueous glycol solution remaining after step (vi).

12. The process of claim 11 wherein at least a portion of the volatile esterified impurities are recycled to the oxidation step (i) to act as an oxidation promoter.

13. The process of claim 12 wherein the volatile esterified impurities are the sole oxidation promoter.

14. The process of claim 12 wherein the volatile esterified impurities comprise esters of 6-formylnaphthoic acid.

15. The process of claim 11 wherein the separating step (vii) includes separating the naphthalene acid ester from the aqueous glycol solution by crystallization and filtration.

16. The process of claim 11 wherein the separating step (vii) includes separating the naphthalene acid ester from the aqueous glycol solution by distillation.

17. A process for purifying a naphthalene dicarboxylic acid by esterification, comprising the steps of:
    (i) mixing a crude naphthalene dicarboxylic acid having impurities with an aqueous solution of an alcohol to form a mixture;
    (ii) heating the mixture to esterify at least a portion of the naphthalene dicarboxylic acid and the impurities to produce a naphthalene dicarboxylic acid ester and volatile esterified impurities,
    (iii) dissolving the naphthalene dicarboxylic acid ester and volatile esterified impurities in an aqueous alcohol solution;
    (iv) removing the volatile esterified impurities by reducing the pressure of the aqueous alcohol solution;
    (v) crystallizing the naphthalene dicarboxylic acid ester from the aqueous alcohol solution; and
    (vi) separating the resultant crystals from the aqueous alcohol solution.

18. The process of claim 17 wherein the alcohol is selected from the group consisting of ethylene glycol, 1,3-propane diol, 1,4-butane diol and mixtures thereof.

19. The process of claim 18 wherein the alcohol is ethylene glycol.

* * * * *